United States Patent [19]

Wenger

[11] 4,114,423

[45] Sep. 19, 1978

[54] DEVICE FOR MEASURING THE DENSITY OF LIQUID AND GASEOUS SUBSTANCES AND METHOD FOR OPERATING THE DEVICE

[75] Inventor: Alfred Wenger, Langenbruck, Switzerland

[73] Assignee: Institut Dr. Ing. Reinhard Straumann AG, Switzerland

[21] Appl. No.: 782,703

[22] Filed: Mar. 30, 1977

[30] Foreign Application Priority Data

Mar. 30, 1976 [CH] Switzerland .................... 3935/76

[51] Int. Cl.² ............................................ G01N 9/00
[52] U.S. Cl. ..................................... 73/30; 73/32 A
[58] Field of Search ............... 73/32 A, 30, 67.2, 579, 73/584

[56] References Cited

U.S. PATENT DOCUMENTS

| 3,117,440 | 1/1964 | Wilner | 73/32 A |
| 3,665,752 | 5/1972 | Piper | 73/32 A |
| 3,874,221 | 4/1975 | Lockie | 73/32 A |
| 4,007,627 | 2/1977 | Stansfeld | 73/32 A |

*Primary Examiner*—Stephen A. Kreitman

*Attorney, Agent, or Firm*—McGlew and Tuttle

[57] ABSTRACT

The device comprises a thin vibratable plate to be introduced into the substances whose density is to be measured, and the plate is held by a holder at a holding point and is vibrated by at least one vibration exciter in operative engagement with the plate. The vibrations of the plate are detected by at least one vibration detector operatively associated with the plate at a point spaced from the point or points at which vibrations are imparted to the plate. An electronic unit is connected to the vibration exciters and the vibration detector and forms therewith an oscillator having an input from the vibration detector and an output supplied to the vibration exciters. The vibration exciters are so positioned with respect to the plate, and so energized by the electronic unit, that the plate vibrates in a manner such that two nodal lines intersect in the range of each holding point at which the plate is supported by a holder. While the plate may have various configurations, it is preferably circular and is so energized that the nodal lines extend diametrically of the plate and intersect at its center, with the center forming the holding point at which the holder supports the plate. The electronic unit includes a meter measuring the periods of the vibration.

16 Claims, 21 Drawing Figures

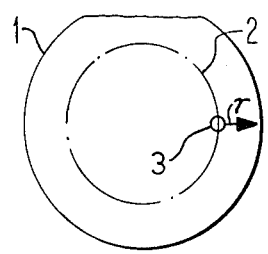
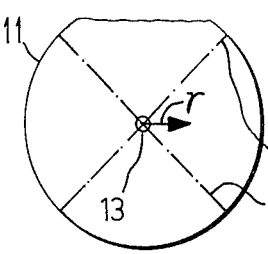
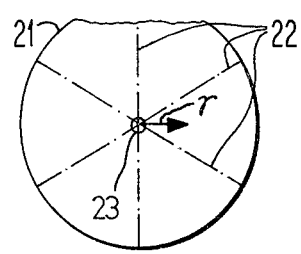
Fig. 1  Fig. 2  Fig. 3
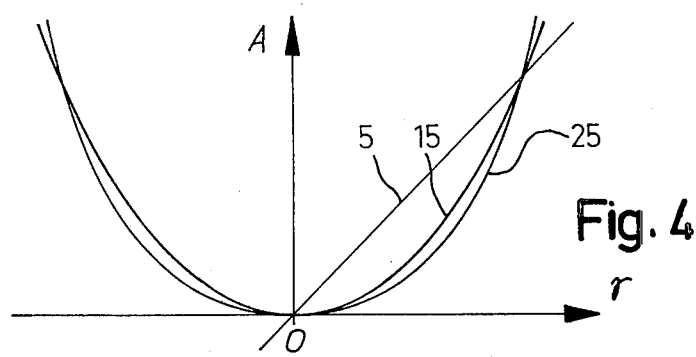
Fig. 4
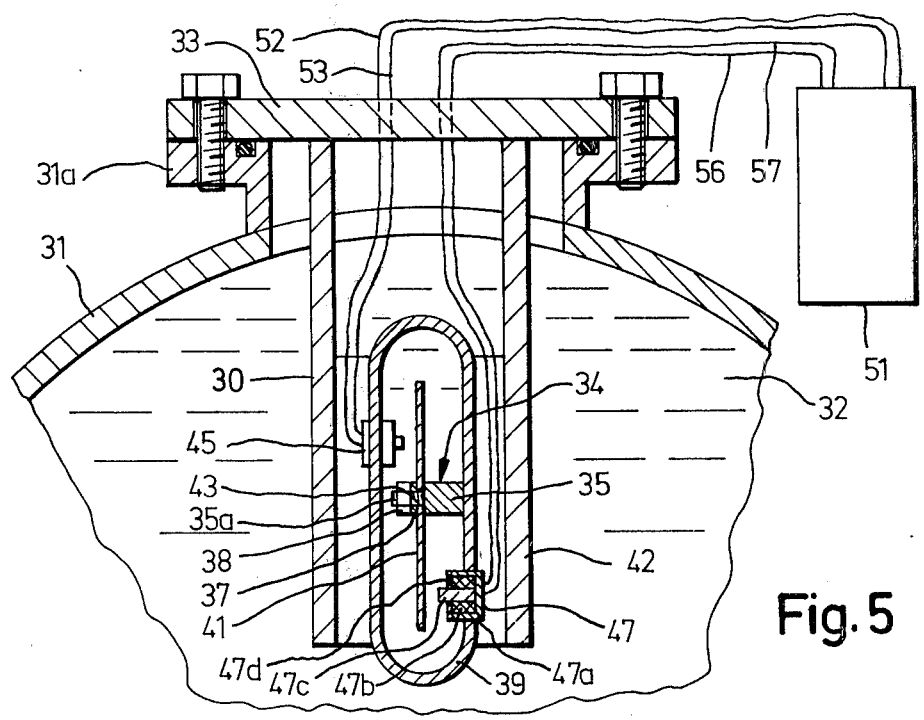
Fig. 5

DEVICE FOR MEASURING THE DENSITY OF LIQUID AND GASEOUS SUBSTANCES AND METHOD FOR OPERATING THE DEVICE

FIELD AND BACKGROUND OF THE INVENTION

This invention is directed to a device for measuring the density of liquid and gaseous substances with a plate, designed to be introduced into the substance to be measured, a holder holding the plate, an electronic unit, at least one vibration exciter connected to the unit and operatively associated with the plate, and at least one vibration detector also connected with the electronic unit and operatively associated with the plate.

In many processes, it is necessary to measure the density of liquid or gaseous substances either continuously or quasi-continuously. It is known that the resonant frequency of a vibrating solid body, which is surrounded by a liquid or a gas, depends on the density of the liquid or gas. Consequently, it is possible to reduce a density measurement to a period measurement or a frequency measurement.

Various devices for measuring the density in accordance with this principle are already known, and the vibrating bodies usually comprise tuning forks or tubular metal bodies. Because of their relatively complicated form, however, such bodies can frequently not be produced with sufficient precision, or can be produced only at great expense. This is particularly the case because the so-called thermocompensating alloys, whose modulus of elasticity is substantially temperature-independent within certain limits, are relatively difficult to process. In addition, the resonant frequencies of these vibration bodies with complicated forms depend not only on the density but, in a manner difficult to control, also on other parameters, particularly the temperature and the holding arrangement. Frequently, it is difficult to mount these complicated vibrating bodies so that the holder does not influence the resonant frequency and does not effect an additional temperature dependence.

An already known device uses a plane circular plate as a vibrating body, and this plate is so excited, at its center, that circular nodal lines are formed during its excitation. The plate is held by a holder, which has three pairs of holding points. The three pairs of points clamp the plate at three holding points or areas arranged on the circular nodal line, these holding points or areas being displaced from each other by an angle of 120°.

However, this known device has only a low measuring accuracy. Since the amplitude of the natural vibration of a free plate increases relatively rapidly inside and outside the circular nodal line, the vibration is influenced, to a relatively great extent, by the three pairs of points, and particularly by the cross-section and surface pressure of the points, so that the measurement can be falsified. This is even more the case, as it is rather difficult in practice to adjust the plate so that the three pairs of points act exactly at the nodal line. Furthermore, material expansions or contractions, caused by temperature variations, can likewise cause a displacement of the nodal line with respect to the pairs of holding points. Besides, this type of holding a plate is not very suitable for rough operation in industrial use.

SUMMARY OF THE INVENTION

The invention is directed to the problem of providing a device which provides a high measuring accuracy and which can be produced at a relatively low cost.

This problem is solved by a device of the above-mentioned type which, in accordance with the invention, is so arranged that each vibration exciter is so positioned, and the electronic unit is so designed, that the plate vibrates in such a way that at least two nodal lines intersect in the range of each holding point where the holder holds the plate.

The invention is based on the fact that the amplitude in the proximity of an intersection of nodal lines extends approximately in a parabola, with the order of the parabola being equal to the number of intersecting nodal lines. If $r$ is the radius measured from the intersection of the nodal lines and $n$ is the number of intersecting nodal lines, the amplitude, in the proximity of the intersection of the nodal lines, is approximately proportional to $r^n$. At the intersection, not only does the amplitude itself have a zero value, but also the derivation of the amplitude for the radius $r$ has a zero value.

However, the amplitude varies in the proximity of an intersection-free nodal line substantially proportional to the distance from the nodal line. Although the amplitude has the value zero in the nodal line, its derivation has not. In other words, the amplitude area intersects the nodal line in an angle.

If the plate is thus held, according to the invention, at an intersection of two or more nodal lines, the holder interferes much less with the vibration than if the plate is held, as in the known prior art, at one point through which there extends only a single nodal line. The contact surface touching the plate at the intersection of the nodal lines therefore can be relatively large and bear tightly on the plate without the vibration frequency of the plate being markedly influenced.

The invention is also directed to a method for operating the device, where a plate is held at at least one holding point, is brought on all sides in contact with a liquid or gaseous substance, and is set into vibrations to measure the density of the substance. In accordance with the method, the plate is so excited that at least two nodal lines intersect in the range of each holding point at which the plate is held.

In a particularly expedient design, the electronic unit has means to feed, to each vibration exciter and at least during one time interval, an alternating current such that the force, generated by the vibration exciter, is displaced forwardly through a phase angle of 45° relative to the vibration rate of the plate in the range of the vibration exciter. It is advantageous that the electronic unit has means for determining the period length of frequency at which the ratio, between the velocity of the plate and the vibration force, is less than the maximum value of this ratio by $\sqrt{2}$.

An object of the invention is to provide an improved device for measuring the density of liquid and gaseous substances.

Another object of the invention is to provide such a device which provides a high measuring accuracy and which can be produced at a relatively low cost.

A further object of the invention is to provide a method of operating such a device.

For an understanding of the principles of the invention, reference is made to the following description of typical embodiments thereof as illustrated in the accompanying drawings.

BRIEF DESCRIPTION OF THE DRAWINGS

In the Drawings:

FIG. 1 is a top plan view of a plate with a circular nodal line;

FIG. 2 is a top plan view of a plate with two nodal lines intersecting at a right angle;

FIG. 3 is a top plan view of a plate with three intersecting nodal lines;

FIG. 4 is a graphic illustration of the course of the amplitude in the proximity of a holding point;

FIG. 5 is a schematic sectional view through a device for measuring the density;

DESCRIPTION OF THE PREFERRED EMBODIMENTS

Figure 6:
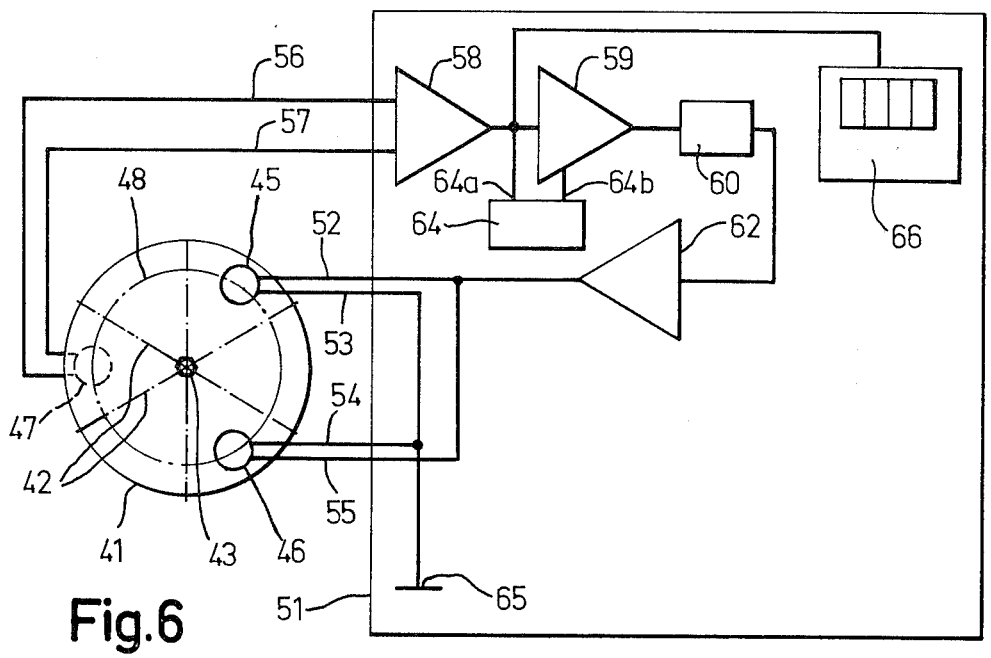
FIG. 6 is a block diagram of the device shown in FIG. 5.

FIGS. 1, 2 and 3 are top plan view of three plane circular and completely freely vibrating plates 1, 11 and 21, respectively, which consequently have free edges. Plate 1 is so excited that a circular nodal line, concentric to plate 1, is formed during vibration. Plate 11 is so excited that two straight nodal lines 12 intersect at a right angle in the center 13 of the plate. Plate 21 is so excited that three nodal lines 22, each constituting a diameter of the plate, are formed and intersect in center 23.

FIG. 4 shows the course of the vibration amplitude A in the proximity of the points 3, 13 and 23 arranged on the nodal lines of the respective plates 1, 11 and 21, along the coordinate axis designated $r$. The amplitude axis A is represented on a much large scale, for the sake of clarity, than is the $r$-axis. In the vibration represented in FIG. 1, the amplitude course is represented approximately by line 5 in FIG. 4. Line 5 intersects the plane defined by the resting plate 1 at point 3 arranged on nodal line 2 at an angle other than zero. In the vibration illustrated in FIG. 2, there is obtained, for the amplitude course in the proximity of intersection 13 of the two nodal lines 12, approximately a parabola of the second order designated, in FIG. 4, at 15. In the proximity of intersection 23 of the three nodal lines 22, there is obtained approximately the amplitude course represented by a parabola of the third order designated with 25 in FIG. 4. For the two parabolas 15 and 25, the derivations $dA/dr$, at the intersections 13 and 23, have the value zero. It follows, therefore, that plates 11 and 21, at the intersections 13 and 23, respectively, and at any time during the vibration, hug the plane extending from the resting plate.

In accordance with the invention, plates 11 and 21 can be held at the intersections 13 and 23, respectively. Since the amplitude areas in the proximity of these points 13 and 23 extend practically parallel to the plane extending from the resting plate, the holder interferes to only a minor extent with the vibration. However, if plate 1, which is not in accordance with the invention, is held at point 3 and other points on nodal line 2, the holder interferes considerably with the vibration in the proximity of these points.

The nodal lines at whose intersection the holder holds the plate preferably should be those which also appear in at least one of the natural vibrations of a plate vibrating completely freely. In such case, the vibrating plate generates no reaction forces acting on the holder. In the presence of a liquid, this important characteristic remains intact if, and precisely only if, the plate has a center of symmetry and is held only at such center of symmetry. The nodal lines of a completely freely vibrating plate can be determined mathematically or experimentally. The experimental determination can be effected, for example, by bedding the plate with its free edges on a foam material and exciting it to vibrations. The nodal lines then can be made visible, for example, by sprinkling a granular material on the plate, as Chladni figures. More accurate determinations can be made of photography or by measuring the local sound reflections.

FIG. 5 shows a device for measuring the density of a liquid 32 which can flow, for example, through a tube 31, having a flange 31a, during the course of an industrial process. A flange 33 is secured on the tube and seals the same tightly from the exterior and, on flange 33, there is secured a carrier 30 protruding into the interior of tube 31. Carrier 30 carries a flat tubular piece 39 which is open at both ends and extends parallel to tube 31. A holder 34 is secured on tubular piece 39 by means of a circular cylindrical pin 35. Pin 35 is formed, on its left end as viewed in FIG. 5, with a threaded bolt 35a which passes through a bore in the mass center, that is, in the center of a plane circular plate 41, whose diameter is substantially greater than its thickness. Plate 41 is clamped on pin 35 by a washer 37 and a nut 38. Holder 34 thus holds plate 41 at holding point 43 in the center of the plate. Plate 41 preferably consists of a rolled thermocompensated alloy, such as used frequently in watch making for the manufacture of spiral springs. By thermocompensation, there is understood that the modulus of elasticity E is substantially constant within a wide temperature range.

The so-called thermoelastic coefficient $\eta$, which is defined by the relation $$\eta = - \Delta E/(E \cdot \Delta\theta) \qquad (1),$$

is then very small. In equation (1), E denotes the variation of the modulus of elasticity for a temperature variation $\Delta\theta$. Thermocompensating alloys can have a thermoelastic coeffecient whose absolute value in the temperature range of $-30°$ C. to $+80°$ C. is less than $5 \cdot 10^{-5}$ deg.$^{-1}$. A known alloy has the following composition: 35–45% Ni, 6–12% Mo, 0.1–1% Be, Balance Fe. Furthermore, it can contain up to 3% Cr or up to 3% Mn+Si.

The device shown in FIG. 5 furthermore has two vibration exciters 45, 46 arranged on one side of the plate, and a vibration detector 47 arranged on the other side of the plate. As can be seen from FIG. 6, these three elements are arranged on a graduated circle 48 concentric with plate 41, and are spaced angularly from each other by 120°. When plate 41 vibrates during a measurement, the three nodal lines 41 are formed, and subdivide plate 41 into six equal sectors. Vibration exciters 45, 46, and vibration detector 47, then lie on the angle-bisectors of respective sectors. To make certain that the anisotropy of plate 41, caused by rolling, influences the vibration as little as possible, plate 41 is so secured that its rolling direction is either parallel to one of the nodal lines 42 or parallel to one of the sector bisectors bisecting the angle between two adjacent nodal lines.

FIG. 5 illustrates detector 47 in a sectional view. The detector has a ferromagnetic pot 47a secured on tubular piece 39, and has, extending along its axis, a core 47c which is surrounded by a winding 47b. The free end of core 47c faces ferromagnetic plate 41. Pot 47a is preferably provided with a non-magnetic cover 47d which seals winding 47b tightly from the exterior.

The device also has an electronic unit 51 whose block diagram is shown in FIG. 6. Vibration exciter 45 is connected by two conductors 52 and 53 with electronic unit 51, and vibration exciter 46 is connected by two conductors 54 and 55 with electronic unit 51. Vibration detector 47 is connected by two conductors 56 and 57 with electronic unit 51. Electronic unit 51 has a differential amplifier 58 with inputs to which are connected the two conductors 56 and 57. The conductors 52 through 57 are conducted through flange 33 in ducts (not shown).

The output of differential amplifier 58 is connected, through an amplifier 59 with controllable amplification, to the input of a phase shifter 60 whose output is connected to the input of an amplifier 62. The output of amplifier 62 is connected, through conductors 52 and 55, respectively, with exciters 45 and 46. The other two conductors 53 and 54 connected to exciters 45 and 46 are connected to chassis 65. Additionally, a comparator 64, containing a reference voltage source, is provided, and has an input 64a connected to the output of amplifier 58. Output 64b of comparator 64 is connected to a control terminal of amplifier 59. A period meter 66 is provided and is connected to the output of differential amplifier 58.

The mode of operation of the device will now be described with reference to FIGS. 7, 8, 9 and 10. When the device is started, plate 41, exciters 45 and 46, detector 47 and electronic unit 51 conjointly form an oscillator. At first, and solely as a mental experiment, it will be assumed that tube 31 contains no liquid and is tightly sealed and evacuated. Furthermore, it will be assumed that phase shifter 60 is bridged. Plate 41 then vibrates with a vacuum-resonant frequency $f_r$. A voltage thus is introduced in the winding of vibration detector 47, and which is in phase with the velocity of plate 41. This voltage is then amplified, by a constant factor, by amplifier 58 and the amplified voltage is supplied to amplifier 59, comparator 64 and period meter 66. Meter 66 then indicates the length of the resonant period. Comparator 64 compares the amplitude or the effective value of the voltage supplied by amplifier 58 with a reference voltage, and controls amplifier 59 so that plate 54 vibrates with a given amplitude. Amplifier 62 then generates a current proportional to the output voltage of amplifier 59, and this current is supplied to exciters 45 and 46. The current supplied to vibration exciters 45, 46 can be so balanced, by means of balancing elements (not shown), that magnetic fields of equal strength are obtained in both vibration exciters 45 and 46. The two vibration exciters are oppositely poled, so that their magnetic fields compensate each other in the range of vibration detector 47. This prevents exciters 45 and 46 from inducing a voltage directly in detector 47. Amplifier 62 works as a current source. Since the force generated by exciters 45 and 46 is in phase with the current, the phase of the force is independent of the phase shift, between voltage and current, produced by the windings of exciters 45 and 46.

The flexural vibration performed by plate 41 is described by a partial differential equation. In the differential equation, there appear terms for the following forces: force of inertia $F_i$, frictional force $F_r$, generated by the friction in the plate material, as well as by the holder, electric restoring force $F_{el}$, and exciting force $F_{exc}$, generated by the exciters. These forces must compensate each other at any time according to the differential equation. The individual elements of plate 41 perform vertical vibrations in operation, the deflection $z$ being a harmonic function of the time $t$. Accordingly, all forces are harmonic functions of the time.

Figure 7:
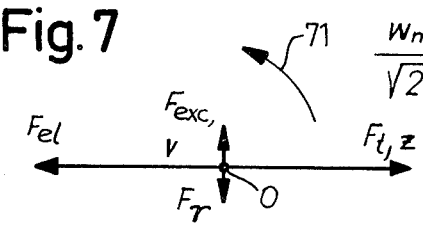
FIG. 7 is a vector diagram illustrating the phase relationships for a plate vibrating, with its resonant frequency, in a vacuum.

The vector diagram of FIG. 7 illustrates the phase relations of a plate vibrating, with its resonant frequency, in a vacuum. Four vectors are shown in FIG. 7, and these vectors rotate, with the same angular velocity, about the coordinate origin O and in the direction indicated by arrow 71. To each of the four vectors, there is assigned one of the four mentioned forces. The inertia force $F_i$ is in phase with the deflection $z$ of the elements of the plate, from the rest position. The exciting force $F_{exc}$ is in phase with the velocity $v$ of the phase elements, and is displaced forwardly by an angle of 90° relative to the force of inertia. The elastic restoring force $F_{el}$ is directed oppositely to the deflection and is thus displaced by 180° relative to the force of inertia $F_i$. The frictional force $F_r$ is directed oppositely to the velocity, and is thus displaced by 180° relative to the exciting force $F_{exc}$.

The voltage induced in vibration detector 47 is proportional to the velocity of the plate elements in contact with vibration detector 47. The windings of vibration exciters 45 and 46 and of vibration detector 47, are now so connected, and the amplifiers of electronic unit 51 are so designed, that the exciting force is, at any time, exactly in phase with the velocity of the plate elements in contact with the vibration exciters 45 and 46. The above-described phase relations are maintained at any time. The fact that the phase angle between the exciting force and the deflection in such mental experiment is 90°, as described above, is tantamount, according to the theory of force vibration, to the finding that the plate vibrates with its vacuum resonant frequency $F_v$. The angular velocity of the four vectors accordingly is equal to the vacuum resonant frequency.

There will now be considered another mental experiment wherein the liquid to be measured is introduced into container 31 and the plate is again set into vibrations. Since now a part of liquid 32 vibrates with plate 41, the force of inertia will be greater than in a vibration in a vacuum. It will be assumed initially that the liquid has no viscosity and that phase shifter 60 is bridged. Plate 41 then vibrates with a resonant frequency $f_m$, which is somewhat lower than the resonant frequency $f_v$ resulting from vibration in a vacuum. The density D of liquid 32 can be calculated by means of the following relation:

$$D = k((T_m/T_v)^2 - 1) \qquad (2)$$

where $k$ denotes a constant, $T_m$ denotes the period length reciprocal to the resonant frequency $f_m$, and $T_v$ denotes the vacuum period length reciprocal to the resonant frequency $f_v$.

Relation or equation (2) applies, however, only to a liquid without viscosity. If the liquid is viscous, the viscosity results not only in a reduction of the quality factor but also in an additional reduction of the resonant frequency. This means that equation (2) yields a too high density. If plate 41 vibrates in a viscous liquid, an additional term appears for the viscous force $F_{vis}$ in the differential equation describing the vibration. In chapter 2, para. 24, of the book "Hydrodynamik" by L. D. Landau and E. M. Lifschitz, Akademie Verlag, Berlin, 1966, there are investigated the relations for the case of a plate which performs a translatory vibration in the plane encompassed by the plate. It can be derived that the viscous force $F_{vis}$ is displaced by 45°, in a natural vibration, relative to the frictional force $F_r$ generated by the internal friction and the holder.

Figure 8:
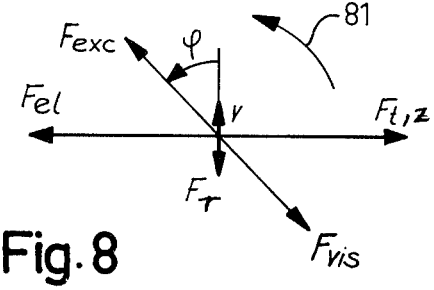
FIG. 8 is a vector diagram illustrating the phase relations for a plate vibrating in a viscous liquid.

This is illustrated in the vector diagram of FIG. 8 in which arrow 81 indicates the direction of rotation of the vectors which generate the forces appearing in the differential equation. If plate 41, its holder 34 and exciters 45, 46 and detector 47 are suitably designed, it can be achieved that the friction force $F_r$ is very small, that is, much smaller than the viscous force $F_{vis}$. If the viscous force $F_{vis}$ is substantially greater than the frictional force $F_r$, the influence of the former can be compensated by displacing the exciting force $F_{exc}$ relative to the velocity $v$ by a phase angle $\phi$ of about 45°. Compared to the deflections, the exciting force $F_{exc}$ is then displaced forward by a phase angle of 135°.

When a real measurement is made, as distinguished from the above mentioned mental experiments, phase shifter 60 is in action and generates a phase shift, so that the exciting force $F_{exc}$ is displaced forwardly by 45° relative to velocity $v$, as described above.

Figure 9:
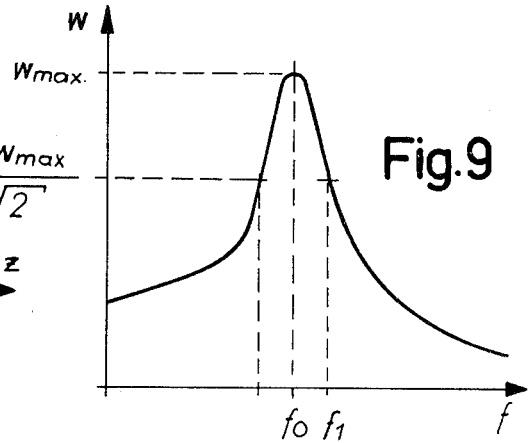
FIG. 9 is a graph illustrating the frequency dependence of the ratio between the velocity and the exciting force.
Figure 10:
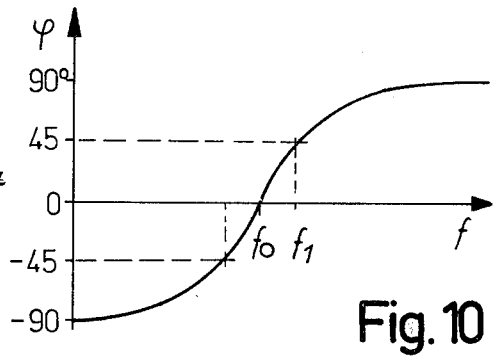
FIG. 10 is a diagram illustrating the frequency dependence of the phase shift between the exciting force and the velocity.

FIG. 9 represents the ratio $w$ between the amplitudes, or effective values, of velocity $v$ and exciting force $F_{exc}$, as a function of the vibration frequency $f$. FIG. 10 represents the magnitude of the phase angle $\phi$ between the exciting force $F_{exc}$ and velocity $v$. At the frequency $f_o$, the ratio $w$ has a maximum value $w_{max}$, and the phase angle $\phi$ has the value 0. At the frequency $f_1$, the ratio $w$ has the value $w_{max}/\sqrt{2}$ and the phase angle $\phi$ has the value 45°. Frequency $F_1$ is the vibration frequency which results when phase shifter 60 is in action, and the exciting force $F_{exc}$ thus is displaced forwardly by 45° relative to velocity $v$. $T_1$ is the period length of the vibration, that is, $T_1 = 1/f_1$.

Plate 41 now vibrates with the frequency $f_1$, for which the exciting force $F_{exc}$ at least approximately compensates the viscous force $F_{vis}$. For the viscous liquid, the density then becomes $$D = k((T_1/T_v)^2 - 1) \qquad (3)$$

where $T_1$ is the measured period length of the vibration, that is, $T_1 = 1/f_1$.

The vacuum period length $T_v$ and the constant $k$ can be determined by means of calibrating liquids. It is thus not necessary to actually make a measurement in a vacuum. But it should be pointed out that formula or equation (3) applies exactly only if the frictional force $F_r$ produced by friction in the plate material and the holder is small, as compared to the viscous force $F_{vis}$. Also, the damping force effected by sound reflection must be small, compared to the viscous force. The sound absorption is proportional to the third power of the ratio: distance of the nodal lines/wavelength of the sound in the liquid.

The error caused by the compressibility is proportional to the second power of the above-mentioned ratio. For determining an exact measuring value, the frequency thus should be low and, accordingly, the mode of vibration of the plate should be of a lower order.

Another source of error will now be discussed. Phase shifter 60 has the effect that the current supplied to vibration exciters 45, 46 is displaced by 45° relative to the voltage supplied by vibration detector 47. Accordingly, the exciting force $F_{exc}$ should be displaced by 45° relative to the velocity.

It is possible, however, that eddy currents are formed in the metallic part of the vibration exciters 45 and 46, and in the segments of plate 41 facing the exciters. These eddy currents can cause a phase shift between the currents supplied to the exciters 45, 46 and the forces generated by them. The exciting force $F_{exc}$ is then no longer displaced exactly by 45° relative to the velocity, so that equation (3) does not yield exactly the correct density. Since the eddy currents depend on the frequency and on the electric resistance, and since the latter depends, in turn, on the temperature, the phase shift between exciting current and exciting force cannot be readily compensated over a wide density and temperature range.

Figure 11:
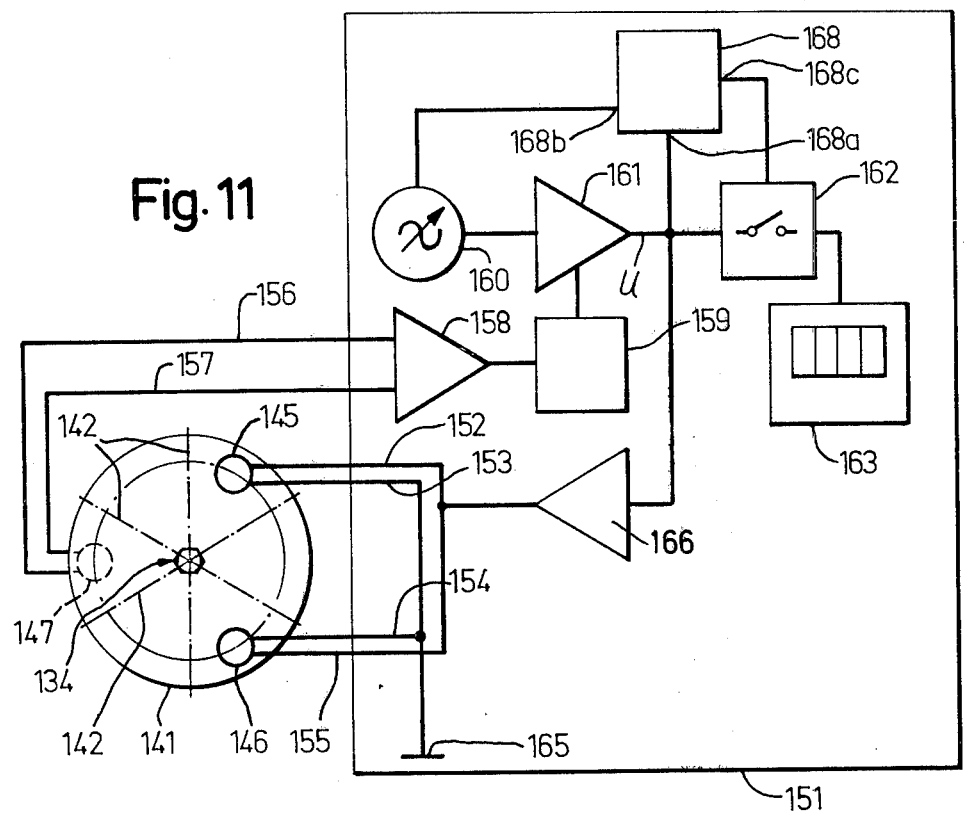
FIG. 11 is a block diagram of another embodiment of the invention.

This source of error is eliminated by the device shown in FIG. 11. Referring to FIG. 11, the device shown therein includes a plate 144 which is held with the holder 134 in a container (not shown), two vibration exciters 145, 146, a vibration detector 147 and an electronic unit 151. Vibration detector 147 is connected, by conductors 156, 157, to the inputs of a differential amplifier 158 in electronic unit 151. The output of amplifier 158 is connected to the input of a voltage comparator 159. Electronic unit 151 also includes a voltage-controlled oscillator 160 whose output is connected to period meter 163 through an electrically controlled switch 162 and also directly to the input of an amplifier 166. The output of amplifier 166 is connected by conductors 152, 153 to one of the winding terminals of the vibration exciters 145, 146, respectively, the other winding terminals of which are connected through respective conductors 153, 154 to chassis 165. A control unit 168 in electronic unit 151 has an input 168a connected to the output of amplifier 161 and an output 168b connected to a control terminal of oscillator 160. Output 168c of control unit 168 is connected to the control terminal of a switch 162. The mode of operation of the device shown in FIG. 11 will now be described. Voltage comparator 159 contains a reference voltage source and controls the amplification of amplifier 161 in such a way that the amplitude or effective value of the voltage, supplied by amplifier 158, is equal to a given nominal value.

Figure 12:
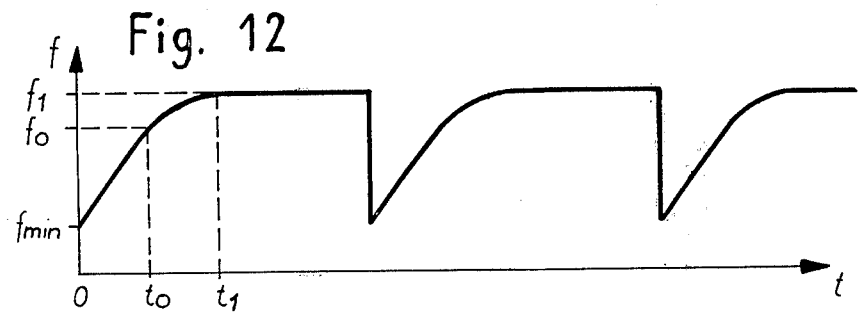
FIG. 12 is a graph illustrating the change with time of the frequency in the operation of the device shown in FIG. 11.
Figure 13:
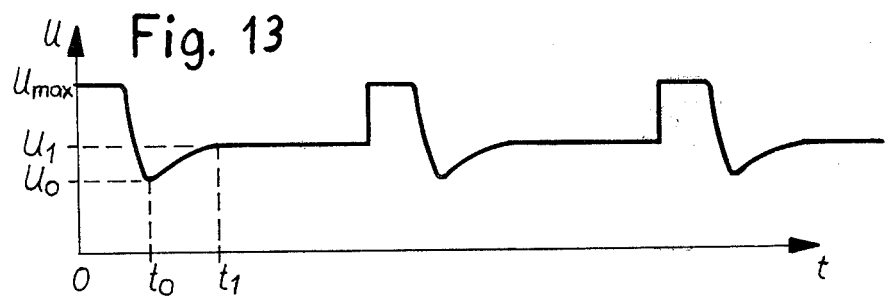
FIG. 13 is a graph illustrating the change with time of a voltage proportional to the amplitude of the exciting force in the operation of the device shown in FIG. 11.

How the density of a liquid is measured quasi-continuously will now be described with reference to FIGS. 12 and 13. Plate 141 is introduced into a tube traversed by the liquid to be measured. FIG. 12 illustrates the time curve of the frequency generated by oscillator 160 after the start of the measurement, and FIG. 13 shows the time curve of the peak value of the output voltage U of the controllable amplifier 161. Amplifier 166 then generates an exciting current which is proportional to output voltage U. At the start of the measurement, the time $t$, in FIGS. 12 and 13, has the value 0, and oscillator 160 generates a vibration with a frequency $f_{min}$, whose magnitude defines the maximum measurable density. Control unit 168 contains means to control oscillator 160 in such a way that the frequency $f$ increases steadily. Since the frequency is, at present, substantially lower than the resonant frequency $f_o$, plate 141 performs vibrations which have only a low vibration velocity, so that the voltage supplied by amplifier 158 is below the given nominal value. Accordingly, amplifier 161 is completely modulated, and its output voltage U is equal to the maximum value $U_{max}$.

When the frequency $f$ approaches the resonant frequency $f_o$, the vibration velocity of plate 141 increases. Voltage comparator 159 now reduces the amplification of amplifier 161 so that voltage U decreases. At the time $t_o$, the frequency attains the value $f_o$. At this frequency, the vibration velocity of plate 141 attains its maximum value, the voltage U accordingly attains the minimum voltage $U_o$. The magnitude of the latter is stored in a storage contained in control unit 168. When the frequency $f$ increases further, voltage U increases again. Control unit 168 contains a comparator which continuously compares the value of the instantaneous voltage with the voltage $U_1$, which is $\sqrt{2}$ — fold amount of voltage $U_o$. Furthermore, it is assumed that the frequency has the value $f_1$. The comparator now has the effect that the frequency is no longer increased. Furthermore, the control unit generates a signal which closes switch 162. The vibration generated by oscillator 160 is also fed to period meter 163 which indicates the magnitude of $T_1 = 1/f_1$.

Since voltage $U_1 = \sqrt{2}\, U_o$, and the exciting current is proportional to voltage U, the ratio $w$ between the vibration velocity and exciting current at the frequency $f_1$ is lower, by $\sqrt{2}$, than the ratio $w_{max}$ at the resonant frequency $f_o$. It follows, from the explanation of FIGS. 8, 9 and 10, that the exciting force $F_{exc}$ is displaced forwardly in this case at the frequency $f_1$ by a phase angle $\phi$ of exactly 45° relative to the velocity of the plate segments in the range of exciters 145 and 146. This phase shift is independent of any eddy currents or of unprovided phase shifts of the electronic unit. The density of the liquid then can be calculated according to equation (3) from the period lengths $T_v$ and $T_1$, or naturally, in an analogous manner from the frequencies $f_v$ and $f_1$.

Control unit 168 contains means for bringing the frequency, after a given time interval, back to the initial value $f_{min}$ and for repeating the measuring process periodically, as indicated in FIGS. 12 and 13. Thus, the density can be measured quasicontinuously. In order to ensure a greater measuring accuracy, a period meter having preferably a counter and a digital reading are used. Naturally, it is also possible to provide a small computer so that the density is indicated directly.

The devices can naturally be used not only for measuring the density of liquids but also for measuring the density of gaseous substances. Plates 41 and 141 can have, for example, a diameter of 40 mm, and their thickness, for the measurement of liquids, can be 0.4 to 0.8 mm and, for the measurement of gases, from about 0.2 to 0.4 mm. The plates can then vibrate with a frequency in the range of 1 to 5 kHz. It is then possible to determine density differences up to 0.001% of the maximum density measurable in the respective range. The deviations of the measured values from the actual value of the density are less than about 0.1% over a wide temperature range.

In the following, there will be described modifications of the support means, exciters and detectors.

Figure 14:
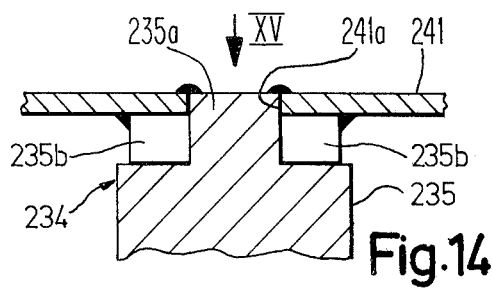
FIG. 14 is a sectional view of a variant of the plate holder.
Figure 15:
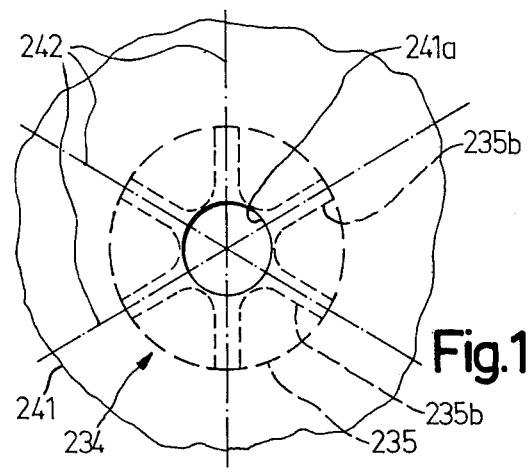
FIG. 15 is a top plan view, in the direction indicated by the arrow XV in FIG. 14.

Referring to FIGS. 14 and 15, a plate 241, with three nodal lines 242, is provided, at its center, with a bore 241a and is held by a holder 234. Holder 234 has a cylindrical carrier 235 which is provided with a smaller diameter cylindrical pin 235a at one end thereof, and which passes through bore 241 and forms, with the latter, a firm seat. From pin 235a, six ribs 235b extend radially outwardly along nodal lines 242. Plate 241 bears on the adjacent edges of ribs 235b and is soldered or welded to the latter, with pin 235a being also soldered or welded to plate 241. The radius of pin 235a and the radial extension of ribs 235b naturally are only a fraction of the radius of plate 241.

Figure 16:
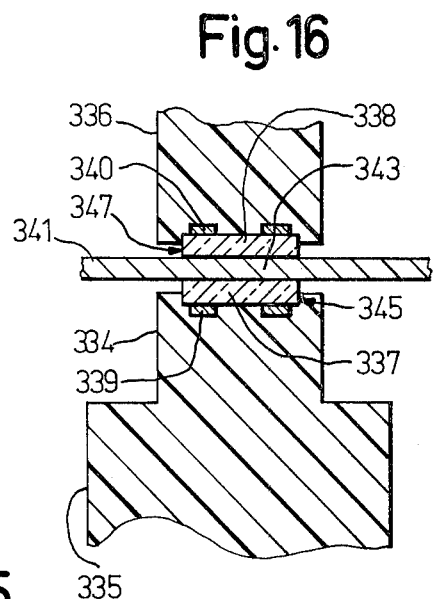
FIG. 16 is a sectional view through another variant of the plate holder, with piezoelectric crystals.

FIG. 16 shows a section through the central portion of a paramagnetic plate 341 which is held, by a holder 334, at a holding point 343, namely, at the center of plate 341. Holder 334 includes two aligned, electrically insulated holding bars 335 and 336 connected with each other by connecting elements (not shown) and pressed toward each other. On the end face of each of the holding bars 335 and 336, facing each other, there is secured a respective piezo-electric crystal 337, 338. Crystals 337 and 338 are provided with six respective electrodes 339 and 340 evenly distributed around a graduated circle. Plate 341 is clamped, at holding point 343, between crystals 337 and 338.

Figure 17:
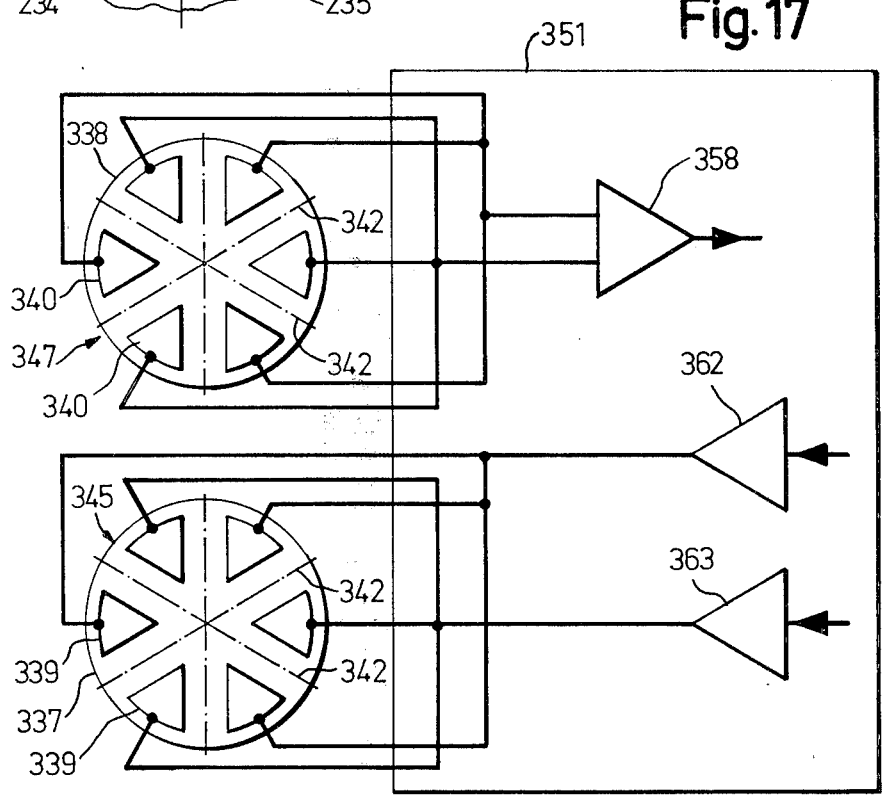
FIG. 17 is a block diagram illustrating the connection arrangement of the piezoelectric crystals.

FIG. 17 illustrates how the electrodes 339 and 340 are connected to the electronic unit. Crystals 337 and 338 are represented side-by-side, in a plan view on a larger scale, for greater clarity. FIG. 17 also shows nodal lines 342 which divide crystals 337 and 338 into equal sectors, and the respective electrodes 339 and 340 are arranged on the bisectors of the angle defined by two adjacent nodal lines 342.

Every second electrode 339 is connected to the output of an amplifier 362 in electronic unit 351, and the remaining three electrodes are connected to the output of an amplifier 363. The two amplifiers 362 and 363 work, in operation, in phase opposition and supply an AC voltage to the connected electrodes 339. Thus, crystal 337 forms, with the six electrodes 339, a vibration exciter 345 with two triple groups of exciter sectors working in phase opposition. Electrodes 340 are likewise combined to two groups of three electrodes, each of which is connected to a respective input of a differential amplifier 358 so that crystal 338 forms, with the six electrodes 340, a vibration detector 347. Only the mentioned amplifiers 362, 363 and 358, of electronic unit 351, have been represented, and electronic unit 351 can be designed in a manner similar to the electronic units 51 and 151.

The use of the paramagnetic plate is particularly advisable when the measuring device is intended for a wide temperature range. A suitable paramagnetic alloy can have a thermoelastic coefficient whose absolute value, in the range of $-30°$ to $+400°$ C., is less than $5 \cdot 10^{-5}$ deg.$^{-1}$. Such an alloy contains, for example, 75% Nb and 25% Zr. The use of a paramagnetic plate has the additional advantage that the measurement is not disturbed by external magnetic fields.

Naturally, there are other possible modifications. For example, the vibration could be excited by magnetostriction. Furthermore, the plate can be so excited that not three, but only two, or perhaps four, nodal lines are formed, as shown in FIG. 2.

It furthermore is possible to use a rectangular plate instead of a round plate and which can be so excited, for example, that a nodal line extends parallel to the longitudinal edges through the plate center, and two additional nodal lines extend transversely of the plate. In this case, there are two intersections of two nodal lines each. The plate could then be held by means of the holder in only one or in each of these two intersections.

However, a rotation-symmetrical plate held at its center has one essential advantage, namely the factor $k$ in equation (2) is constant if, and precisely only if, the shape of the plate deformation taking place during oscillation is independent of ambient flow media. This is the case, with great accuracy, with the circular plate with diametrically extending nodal lines, and held at the center of symmetry, because the vibratory deformation is determined to a great extent by the symmetry conditions which are not changed by the flow medium.

Figure 18:
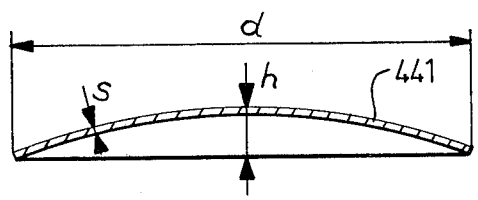
FIG. 18 is a sectional view of a curved plate.

The plates also could be slightly curved instead of plane, so that they form a flat substantially spherical or paraboloid shell. Since such a curvature increases the bending resistance, the plates can be made of thinner material. This results in a greater sensitivity, which can have a particularly advantageous effect in the measurement of gases. An example of a curved plate is shown at 441 in FIG. 18. The thickness of plate 441 is designated $s$, the maximum diameter $d$ and the height of the curvature $h$. The curvature of the plate is so selected that the unbalance $$h / \sqrt{ds} < 2 \qquad (4)$$

is satisfied.

Figure 19:
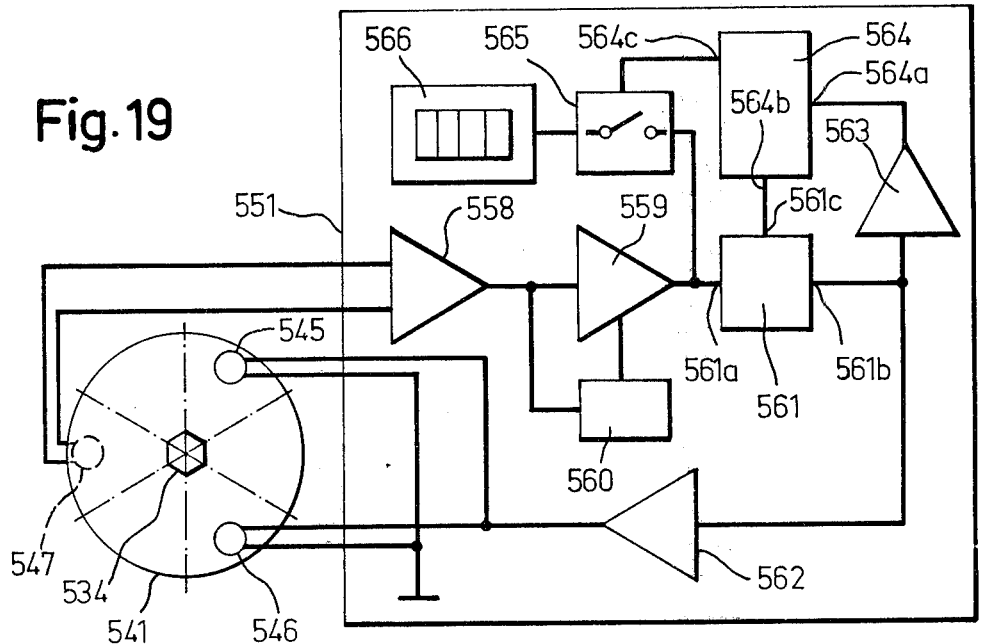
FIG. 19 is a block diagram of another variant of the electronic unit.

In the embodiment of the invention shown in FIG. 19, a plate 541 is held by a holder 534 and associated with vibration exciters 545, 546, a vibration detector 547 and an electronic unit 551. Vibration detector 547 is connected to the inputs of a pre-amplifier 558 whose output is connected to the input of an amplifier 559 with controllable amplification, and to the input of a comparator 560. The output of comparator 560 is connected to a control terminal of amplifier 559, and controls its amplification in such a way that the voltage supplied by vibration detector 547 has a constant amplitude.

The output of amplifier 559 is connected to the input 561a of a controllable phase shifter 561, whose output is connected to the input of an amplifier 562 having an output connected to vibration exciters 545 and 546, and which works as a controllable current source. Output 561b of phase shifter 561 is also connected to the input of an amplitude meter 563 whose output is connected to the input 564a of control unit 564 having an output 564b connected to control terminal 561c of phase shifter 561 and an output 564c connected to the control terminal of an electronic switch 565. Switch 565 connects the output of amplifier 559 to a period meter 566.

Figure 20:
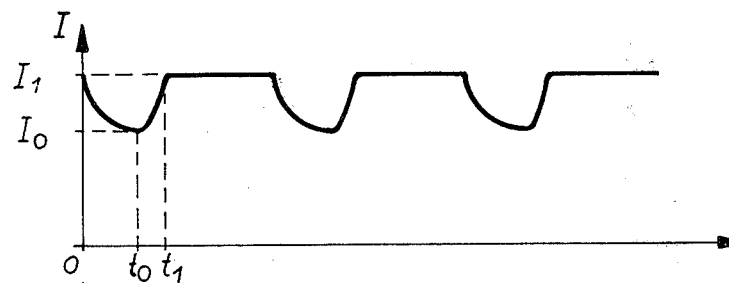
FIG. 20 is a graph illustrating the change with time of the amplitude of the exciting current.
Figure 21:
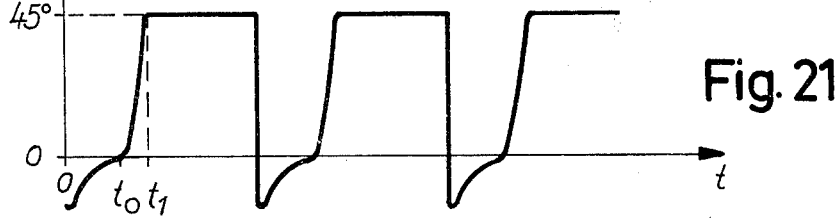
FIG. 21 is a graph showing the change with time of the phase shift between the exciting force and the velocity.

The mode of operation of the electronic unit 551 will now be described with reference to FIGS. 20 and 21. In conjunction with plate 541, electonic unit 551 forms an oscillator. At the time $t = 0$, phase shifter 561 effects a phase shift such that the phase of the exciting force $F_{exc}$ is displaced slightly backwardly relative to the vibration velocity of plate 541. The phase angle $\phi$ is then negative. Control unit 564 now controls phase shifter 561 in such a way that the phase angle $\phi$ increases and has, at the time $t = t_o$, the value 0. The amplitude of the exciting current I drops to the minimum value $I_o$.

Control unit 564 contains means for determining the minimum amplitude of the output voltage of phase shifter 561 proportional to the exciting current I, and a storage for storing this minimum value. Control unit 564 also contains a comparator, and now controls phase shifter 561 in such a way that phase angle $\phi$ increases until the exciting current I has the value $I_1$ which is equal to $\sqrt{2} I_o$. Phase angle $\phi$ is then $+45°$, and the above-mentioned ratio $w$ is less than the maximum value $w_{max}$ by $\sqrt{2}$. Control unit 564 now controls the phase shifter in such a way that phase angle $\phi$, as well as exciting current I, remains constant during a given time interval and closes switch 565 during this time interval. Period meter 566 then measures the period length $T_1$ of the vibration, from which the density can be calculated in the manner described hereinbefore. At the end of the given time interval, control unit 564 reopens switch 565 and restores phase shifter 561 to its initial value. The process is now repeated periodically and the period length is measured in each time interval in which the phase angle is 45°.

If the time intervals between the individual measurements are to be kept as short as possible, electronic unit 551 can be modified slightly. Control unit 564 then is so designed that phase angle $\phi$ is not negative at the start of the measurement, but is just 0. This means that each measurement is started at the time $t_o$ when the ratio $w$ has its maximum value $w_{max}$. This maximum value is now stored again, and phase angle $\phi$ is constantly increased until $w = w_{max}/\sqrt{2}$. Then the phase angle is kept constant during a time interval, and the period length is measured. Subsequently, control unit 564 restores phase shifter 561 to its initial value.

As explained in that part of the description preceding the description of the embodiment of FIG. 11, the exciting force is not always exactly in-phase with the exciting current. If provisions are made, in the variant just described, to set the phase shifter at the start of each measuring operation to an initial position, in which the phase angle between the exciting current and the voltage supplied by vibration detector 547 has the value 0, it is possible that the actual phase angle $\phi$ between the velocity $v$ and the exciting force $F_{exc}$ differs somewhat from 0. But since the ratio $w$ has its maximum at the phase angle zero, as can be seen from FIGS. 9 and 10, and consequently a zero rise, its value differs very little from the maximum value, when the phase angle deviates slightly from zero. If the phase angle is now increased until the ratio $w$ is lower than the stored maximum value of the ratio by $\sqrt{2}$, the resulting phase angle will differ only slightly from 45°. Accordingly, the error remains very small, despite any deviation of the initial phase angle from zero.

Electronic unit 551 can be so modified, to increase the measuring velocity, that, instead of the amplitude of velocity $v$, the amplitude of the exciting force is kept constant. In this case, the input of amplitude meter 563 would be connected to the output of amplifier 558, and control unit 564 would be so modified that it determines the ratio $w$ from the now variable velocity $v$. Controllable amplifier 559, comparator 560 and amplifier 562, working as a current source, would then be so designed that an alternating current, of constant amplitude, is fed to vibration exciters 545 and 546.

While specific embodiments of the invention have been shown and described in detail to illustrate the application of the principles of the invention, it will be understood that the invention may be embodied otherwise without departing from such principles.

What is claimed is:

1. In a device for measuring the density of liquid and gaseous substances, and of the type including a plate to be introduced into the substance to be measured, at least one holder holding the plate at a holding point, an electronic unit, at least one vibration exciter connected to the electronic unit and operable to vibrate the plate, and at least one vibration detector connected to the electonic unit and operable to detect vibrations of the plate, the improvement comprising, in combination, a plate to be introduced into the substance to be measured; a holder holding said plate at only a single holding point; an electronic unit; at least one vibration exciter connected to said electronic unit and operable to vibrate said plate; and a vibration detector connected to said electronic unit and operable to detect vibrations of said plate; each vibration exciter being so positioned relative to said plate and so energized by said electronic unit acting, in conjunction with said exciters and said detector, as an oscillator, as to vibrate said plate in a manner such that two nodal lines intersect in the range of said single holding point.

2. In a device for measuring the density of liquid and gaseous substances, the improvement claimed in claim 1, in which said plate has a center of symmetry and said single holding point is at such center of symmetry.

3. In a device for measuring the density of liquid and gaseous substances, the improvement claimed in claim 2, including piezo-electric crystals bearing against said plate at said holding point and divided into sectors, each provided with a respective electrode; one crystal forming, with its electrodes, a vibration exciter, and the other crystal forming, with its electrodes, a vibration detector.

4. In a device for measuring the density of liquid and gaseous substances, the improvement claimed in claim 1, in which said intersecting nodal lines are nodal lines which also appear in at least one of the natural vibrations of the completely freely vibrating plate.

5. In a device for measuring the density of liquid and gaseous substances, the improvement claimed in claim 1, in which said plate is rotationally symmetrical; said electronic unit being so designed, and each vibration exciter being so positioned, that said nodal lines are diameters of said plate and divide said plate into equal circular sectors.

6. In a device for measuring the density of liquid and gaseous substances, the improvement claimed in claim 5, in which said nodal lines subdivide said plate into six circular sectors.

7. In a device for measuring the density of liquid and gaseous substances, the improvement claimed in claim 5, in which said plate is rolled with the rolling direction being parallel to a nodal line.

8. In a device for measuring the density of liquid and gaseous substances, the improvement claimed in claim 5, in which said plate is rolled with the rolling direction parallel to one of the lines bisecting the angle between two adjacent nodal lines.

9. In a device for measuring the density of liquid and gaseous substances, the improvement claimed in claim 1, in which said electronic unit includes means supplying an alternating current to each vibration exciter during at least one time interval and in a manner such that the force generated by the vibration exciter is displaced in a leading direction, through a phase angle of 45°, relative to the vibration velocity of the plate in the range of the vibration exciter.

10. In a device for measuring the density of liquid and gaseous substances, and of the type including a plate to be introduced into the substance to be measured, at least one holder holding the plate at a holding point, an electronic unit, at least one vibration exciter connected to the electronic unit and operable to vibrate the plate, and at least one vibration detector connected to the electronic unit and operable to detect vibrations of the plate, the improvement comprising, in combination a plate to be introduced into the substance to be measured; a holder holding said plate at only a single holding point; an electronic unit; at least one vibration exciter connected to said electronic unit and operable to vibrate said plate; and a vibration detector connected to said electronic unit and operable to detect vibrations of said plate; each vibration exciter being so positioned relative to said plate and so energized by said electronic unit acting, in conjunction with said exciters and said detector, as an oscillator, as to vibrate said plate in a manner such that two nodal lines intersect in the range of said single holding point; said electronic unit including means supplying an alternating current to each vibration exciter during at least one time interval and in a manner such that the force generated by the vibration exciter is displaced in a leading direction, through a phase angle of 45°, relative to the vibration velocity of the plate in the range of the vibration exciter; a control unit operable to vary the frequency and such phase angle during a time interval in each measurement; and means operable to determine one of the period lengths and frequency at which the ratio, between the velocity of the plate and the exciting force, is less than the maximum value of such ratio by a factor $\sqrt{2}$.

11. In a device for measuring the density of liquid and gaseous substances, the improvement claimed in claim 10, including an oscillator in said electronic unit connected with said control unit and controlled by said control unit; and means in said control unit operable to increase the frequency of said oscillator constantly during each measurement, starting from a minimum value, to store the maximum value of the ratio between the velocity of said plate and the exciting force, and to maintain the frequency constant during a time interval when said ratio is less than its maximum value by a factor $\sqrt{2}$.

12. In a device for measuring the density of liquid and gaseous substances, the improvement claimed in claim 10, including a phase shifter in said electronic unit connected with said control unit and controlled by said control unit; and means in said control unit operable to first increase the phase angle constantly, starting from a minimum value, until the ratio between the velocity of said plate and the exciting force is less than the maximum value of said ratio by a factor $\sqrt{2}$, and then to maintain the phase angle constant during a time interval.

13. In a method for measuring the density of liquid and gaseous substances by introducing, into the substance to be measured, a plate so that it is in contact, on all surfaces, with the substance, with the plate being held at at least one holding point and set into vibration to measure the density of the substance, the improvement comprising the steps of holding said plate at only a single holding point; exciting said plate into vibration at excitation points spaced from said single holding point such that at least two nodal lines intersect in the range of said single holding point; and detecting the vibrations of said plate at a detecting point spaced from the excitation points and from said single holding point.

14. In a method for measuring the density of liquid and gaseous substances, the improvement claimed in claim 13, including the step of determining one of the period lengths and frequency at which the exciting force, serving to vibrate the plate, is displaced forwardly, through a phase angle of substantially 45°, relative to the velocity of the plate segments acted upon by the exciting force.

15. In a method for measuring the density of liquid and gaseous substances, the improvement claimed in claim 13, including determining the maximum value of the ratio between the vibration velocity and the exciting force, and one of the period length and frequency of the vibration, at which the value of the ratio between the vibration velocity and the exciting force is less than the maximum vlaue of such ratio by a factor $\sqrt{2}$.

16. In a method for measuring the density of liquid and gaseous substances, the improvement claimed in claim 13, including holding the plate in the range of the intersection of nodal lines, which nodal lines also appear in at least one of the natural vibrations of the completely freely vibrating plate.

* * * * *